United States Patent [19]

Muff

[11] 4,367,577
[45] Jan. 11, 1983

[54] EXTRACTOR FOR REMOVING BROKEN TUBING TIPS FROM CATHETER HUBS

[76] Inventor: Nicholas S. Muff, 1044 Rolling Ridge Dr., Sedro Woolley, Wash. 98284

[21] Appl. No.: 214,421

[22] Filed: Dec. 8, 1980

[51] Int. Cl.³ ............................................. B23P 19/04
[52] U.S. Cl. ..................................... 29/234; 29/264; 29/267; 81/302
[58] Field of Search ................... 81/302; 29/264, 267, 29/268, 234

[56] References Cited

U.S. PATENT DOCUMENTS

| 206,795 | 8/1878 | Jarecki . | |
|---|---|---|---|
| 1,563,840 | 12/1975 | Dirks | 29/248 |
| 1,629,953 | 5/1927 | Foote | 29/248 |
| 2,488,036 | 11/1949 | Pofcher | 29/256 |
| 2,519,024 | 8/1950 | Collett | 81/302 |
| 3,390,561 | 7/1968 | Finck, Jr. . | |
| 3,540,106 | 11/1970 | Goldman | 81/302 |
| 3,677,129 | 7/1972 | Lyon . | |
| 3,823,462 | 7/1974 | Kanda . | |
| 3,916,907 | 11/1975 | Peterson . | |
| 4,018,110 | 4/1977 | Spriggs . | |
| 4,050,464 | 9/1977 | Hall . | |
| 4,086,799 | 5/1978 | Brendle | 81/302 |

Primary Examiner—James L. Jones, Jr.
Attorney, Agent, or Firm—Christensen, O'Connor, Johnson & Kindness

[57] ABSTRACT

A tool (10) for extracting a tubing segment (52) from a member (50) in which the tubing segment is inserted includes first and second handles (12, 14) terminating at adjacent ends in respective first and second jaws (16, 18). The handles are pivotally coupled and are configured so that, as the handles are swung toward each other, the jaw portions are separated. The jaws have mutually aligned apertures (30, 32) through which extends a rod or needle (44) having a first end (44a) extending beyond one of the jaws and a second end (44b) extending beyond the other of the jaws. The second end of the rod is externally threaded. A knob (46) is affixed to the first end of the rod for the purpose of threading the threaded end of the rod into the tubing segment and for bearing against the surface of the jaw adjacent the first end of the rod so that, as the jaws are separated, the threaded end of the rod is drawn through the aperture, drawing with it the tubing segment to be removed. The other jaw bears against the member to prevent its movement while the tubing segment is removed.

11 Claims, 4 Drawing Figures

EXTRACTOR FOR REMOVING BROKEN TUBING TIPS FROM CATHETER HUBS

BACKGROUND OF THE INVENTION

The present invention broadly relates to an apparatus for extracting a tubing segment from a member in which said tubing segment is inserted, and more particularly to a tool for assisting in the removal of broken tubing and needle tips from catheter hubs.

Catheters are many times placed into the vein of a medical patient, for example, to maintain a patient's nutrition via intravenous feeding. Catheters normally terminate in an entrance hub exterior of the patient's skin. The tip of a piece of tubing running from a source of, for example, intravenous solution is removably inserted in the catheter hub to couple the catheter with the source of fluid. Many times the tubing must be removed and replaced with the tips of syringe needles and the like. In any event, the sticky, high-sugar solutions employed many times function as an adhesive and cement the tubing tip to the catheter entrance hub. Many times then, when an attempt is made to remove the tubing tip from the catheter hub, the tubing tip will fracture at the outer edge of the hub and remain lodged in the hub.

In the past, such a mishap has required removal of the catheter from the patient, entailing patient discomfort and expense in time and money for removal and replacement. In some instances, the catheter cannot be readily removed, as when a Hickman catheter that actually extends into the heart is employed. In the latter instance, past practice has required that the hub containing the tubing tip be severed from the catheter and a new hub spliced onto the catheter. Considerable effort is involved in making such a splice and results in less than a satisfactory substitute.

Accordingly, it is a broad object of the present invention to eliminate the need to replace catheters or splice new hubs onto exisiting catheters when a tubing tip is broken off and lodged in the catheter hub. More specifically, it is an object of the present invention to provide a simple, easily manipulable, relatively inexpensive apparatus for removing the broken tip from a catheter hub, and more specifically, to provide such an apparatus that will achieve its intended purpose with a minimum of or no discomfort to the patient.

SUMMARY OF THE INVENTION

The foregoing objects, and other objects that will become apparent to one of ordinary skill after reading the following specification, provide an apparatus for extracting a tubing segment from a member in which the tubing segment is inserted. The apparatus includes first and second jaws and means mounting the first and second jaws for relative movement toward and away from each other between a first position adjacent each other and a second position spaced from each other. A means is provided for manipulating the jaws between the first and second positions. A grasping means coacts with the first jaw portion for insertion into and grasping of a tubing segment. A coaction means is provided on the second jaw portion for coacting with the member into which the segment is inserted so that when said jaw portions are moved from said first position to said second position a relative axial force is exerted on said tubing segment and said member to remove said tubing segment from said member. In a preferred embodiment, the jaws are formed on adjacent ends of a pair of handles. The handles are mounted for relative swinging movement so that as the ends of the handles opposite from the jaws are swung toward each other, the jaw portions are separated.

BRIEF DESCRIPTION OF THE DRAWINGS

A better understanding of the present invention can be derived from a reading of the ensuing specification in conjunction with the accompanying drawings wherein.

DETAILED DESCRIPTION OF THE INVENTION

Figure 1:
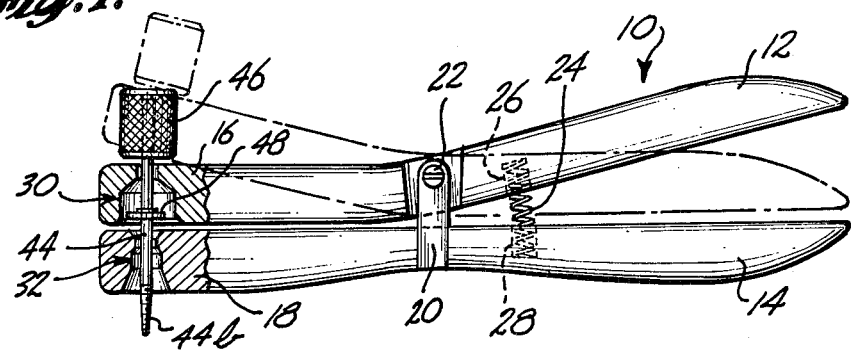
FIG. 1 is a side elevation view in partial section of a tool constructed in accordance with the present invention for extracting a tubing segment from a member in which the segment is inserted.

Referring first to FIG. 1, an extraction tool 10 constructed in accordance with the present invention includes an upper handle 12 and a lower handle 14. A pair of jaws 16 and 18 are integrally formed on adjacent ends of the handles 12 and 14. A yoke 20 extends transversely upwardly from a location on the handle 14 between the free end of the handle and the jaw 18. The upper end of the yoke 20 is pivotally coupled by a pivot pin 22 to a corresponding location on the upper handle 12. While the lower handle 14 and integral jaw 18 are configured so that they lie on a relatively straight line, the upper handle 12 diverges away from the handle 14 as it extends away from the pivot pin 22 when the jaws 16 and 18 are positioned adjacent each other. Thus, when the two handles 12 and 14 are moved toward each other, the jaws 16 and 18 swing away from each other. Likewise, when the handles 12 and 14 are moved away from each other, the jaws 16 and 18 swing toward each other into juxtaposed relationship. A compression coil spring 24 has its respective ends mounted in aligned bores 26 and 28 in respective handles 12 and 14 adjacent the yoke 20, but on the opposite side of the yoke from the jaws. The bores 26 and 28 and thus the spring 24 are aligned such that the coil spring forces the handles 12 and 14 away from each other, thus biasing the jaws 16 and 18 toward each other into juxtaposed relationship.

Figure 2:
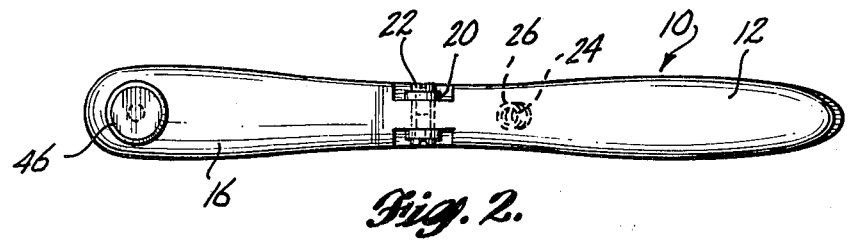
FIG. 2 is a plan view of the tool.

Still referring to FIGS. 1 and 2, the jaws 16 and 18 when in position adjacent each other carry axially aligned bores generally designated 30 and 32. The axis of the bore lies generally in the place of swinging movement of the jaws 16 and 18, and particularly in a plane that cuts through the jaws and is generally orthogonally oriented relative to the axis of the pivot pin 22. The bore 30 in the upper jaw 16 has a small diameter upper portion 34 and flares into a larger diameter lower portion 36. The upper portion 38 of the bore 32 through the lower jaw 18 has a relatively small diameter flaring into a medium diameter portion 40 and thereafter flaring outwardly to the bottom surface of the jaw 18 to form a frustoconically shaped bottom portion or recess 42.

An extraction needle 44 is axially positioned in the bores 30 and 32 for upwardly and downwardly reciprocating movement. The needle 44 has a diameter that is smaller than the smallest diameter of the bores 30 and 32 so that it can be slightly canted relative to the bore axes. The upper end 44a of the extraction needle extends above the jaw 16. A knurled knob 46 is securely affixed to the upper end 44a of the needle 44. A retention washer 48 is affixed to the central portion of the needle 44. The washer has a diameter less than the diameter of the lower portion 36 of bore 30 but larger than that of the upper portion 34 of bore 30. The washer bears against the flared portion of bore 30 as the needle is moved upwardly, preventing the needle from being removed from the bore.

The lower end 44b of the needle 44 extends below the lower portion of jaw 18 when the jaws 16 and 18 are positioned adjacent each other. The lower portion 44b is generally conically shaped and carries threads extending from its lower tip upwardly to a location spaced above the tip. When the handles 12 and 14 are squeezed together against the bias of spring 24, the upper surface of the upper jaw 16 bears against the knob, virtually retracting the lower end 44b of the needle into the bore 32 in the lower jaw 18 as the jaws separate.

Figure 3:
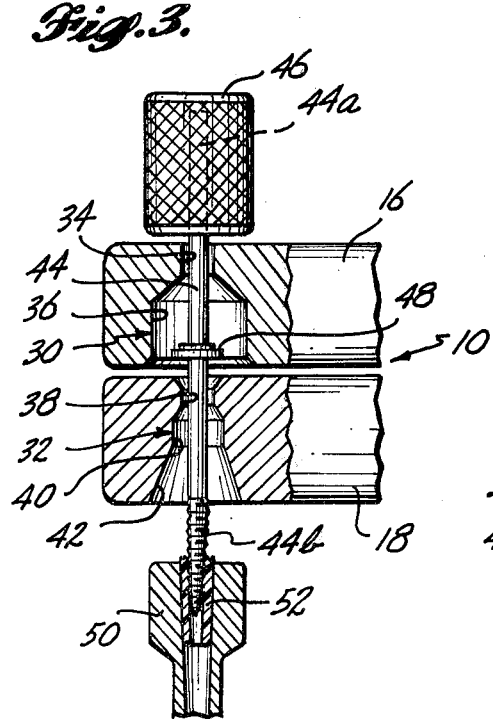
FIG. 3 is an enlarged sectional view of the jaw portion of the tool showing the extraction needle inserted into a tubing segment in preparation for extracting the tubing segment.
Figure 4:
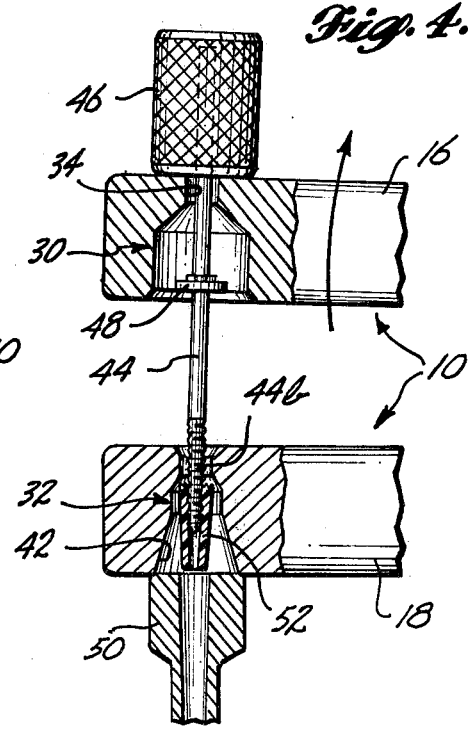
FIG. 4 is a view similar to FIG. 3 showing the segment removed from a catheter hub.

Referring to FIGS. 3 and 4, in operation, the lower portion of jaw 18 is positioned adjacent a catheter hub 50 or other device from which a tubing segment 52, needle segment, or other hollow member is to be removed. The lower threaded portion 44b of the extraction needle 44 is then inserted into the bore of the tubing segment 52. The knurled knob 46 is turned to thread the lower portion 44b into the tubing segment 52 to thus temporarily secure the tubing segment to the needle. The handles 12 and 14 are then gently squeezed positioning the lower surface of the jaw 18 adjacent the upper end of the catheter hub 50 and drawing it slightly into the frustoconically shaped lower portion 42 of the bore 32, thus tending to center the hub 50 in the bore 32. As the upper end of the hub 50 contacts the walls of the frustoconically shaped lower portion 42, the hub is retained in place. As the operator continues to squeeze the handles 12 and 14, the jaw 16 separates further from the jaw 18, causing the bottom end of the knurled knob 46 to bear against the upper portion of the jaw 16, thus drawing the needle away from the hub 50. As the needle 44 is drawn away from the hub 50, the broken-off tubing segment 52 is extracted from the bore of the hub.

As can be seen, the tool can be utilized and manipulated in a way to extract broken tubing segments, needle tips, and the like from catheter hubs or other receptacles with little or no disturbance or displacement of the catheter hub itself. Thus, the device can quickly and easily recoup the use of a hub which otherwise might have been lost, with very little discomfort and cost to the patient. One of ordinary skill after reading the foregoing specification will be able to effect various changes, substitutions of equivalents, and other alterations without departing from the broad concepts of the invention, which has been described herein in relation to a preferred embodiment. Accordingly, it is intended that the scope of the Letters Patent granted hereon be limited only by the definition contained in the appended claims and equivalents thereof.

The embodiments of the invention in which an exclusive property or privilege is claimed are defined as follows:

1. An apparatus for extracting a tubing segment from a member in which said tubing segment is inserted comprising:
   first and second handles terminating at one end thereof in respective first and second jaw portions, said second jaw portion including an aperture,
   means joining said handles for relative swinging movement so that, as the other ends of said handles are swung toward each other, said jaw portions are separated,
   grasping means coacting with said first jaw portion for insertion into and grasping said tubing segment,
   coaction means on said second jaw portion for coacting with said member so that relative axial force is exerted on said tubing segment and said member as said jaw portions are separated, said coaction means defining a receptacle for receiving an extracted tubing segment, said receptacle communicating with said aperture, said grasping means extending through said aperture and said receptacle.

2. The apparatus of claim 1 wherein the cross-sectional area of said aperture is smaller than the cross-sectional area of said receptacle, the cross-sectional area of said aperture being only large enough to accept said grasping means.

3. The apparatus of claim 1 further comprising:
   means associated with said handles for biasing said jaw portions toward each other.

4. The apparatus of claims 2 or 3 wherein said first jaw portion has an aperture therethrough, said apertures in said first and said second jaw portions being aligned along a line intersecting said handles, said grasping means comprising a rod extending through said apertures, said rod having a first end extending beyond said first jaw portion and a second end extending beyond said second jaw portion, said second end being externally threaded.

5. The apparatus of claim 4 wherein said threaded end is conically shaped so as to be threadably insertable into tubing segments having various internal diameters.

6. The apparatus of claim 5 further comprising:
   a knob affixed to the first end of said rod for grasping with the fingers to apply a torque to the rod in order to thread said second end into a tubing segment.

7. The apparatus of claim 6 wherein said coaction means comprises the portion of said second jaw portion surrounding the aperture therein.

8. The apparatus of claim 7 wherein said member is circular in cross section and wherein the aperture in said second jaw portion is radially outwardly flared as it extends toward said second end of said rod so that said member is centered in said aperture as said jaws are separated.

9. The apparatus of claim 8 further comprising means for retaining said rod in said aperture in said first jaw.

10. The apparatus of claim 1 wherein said grasping means comprises a rod having a first end and a second end, the first end of said rod being mounted for rotation on said first jaw portion, the second end of said rod extending toward and beyond said second jaw portion, the second end of said rod being threaded.

11. The apparatus of claim 10 wherein said coaction means comprises a surface on said second jaw portion that is so configured to engage a portion of said member surrounding a tubing segment when said threaded second end of said rod is inserted in a tubing segment.

* * * * *